United States Patent [19]

Stahly et al.

[11] Patent Number: 4,511,729

[45] Date of Patent: * Apr. 16, 1985

[54] NUCLEOPHILIC SUBSTITUTION PROCESS

[75] Inventors: G. Patrick Stahly; Barbara C. Stahly, both of Baton Rouge, La.

[73] Assignee: Ethyl Corporation, Richmond, Va.

[*] Notice: The portion of the term of this patent subsequent to Oct. 9, 2001 has been disclaimed.

[21] Appl. No.: 474,137

[22] Filed: Mar. 10, 1983

Related U.S. Application Data

[63] Continuation-in-part of Ser. No. 452,616, Dec. 23, 1982, , which is a continuation-in-part of Ser. No. 373,633, Apr. 30, 1982.

[51] Int. Cl.$^3$ .............................................. C07C 79/46
[52] U.S. Cl. ..................................... 560/020; 560/21; 560/23; 560/9; 562/431; 562/435
[58] Field of Search .......................... 560/20, 21, 23, 9; 562/431, 435

[56] References Cited

PUBLICATIONS

Golinski, J. et al., Tetrahedron Letters, No. 37, pp. 3495–3498, 1978.
J. O. Chem., 1980, 45, 1534–1535.
Int. Conf. Biotechnol. Biol. Acta. Nat. Pred. (Proc.) 1st 1981, Issue 2, pp. 480–490.

Primary Examiner—Paul J. Killos
Attorney, Agent, or Firm—Donald L. Johnson; John F. Sieberth; Patricia J. Hogan

[57] ABSTRACT

Nitrophenoxy- or nitrophenylthiobenzeneacetic acid esters are prepared by reacting a nitrophenoxy- or nitrophenylthiobenzene with an alpha,alpha-disubstituted acetic acid ester in an inert solvent and in the presence of a base. The products are useful as intermediates for the synthesis of pharmaceuticals, such as fenoprofen.

17 Claims, No Drawings

NUCLEOPHILIC SUBSTITUTION PROCESS

CROSS-REFERENCE

This application is a continuation-in-part of copending application Ser. No. 452,616, filed Dec. 23, 1982, which in turn is a continuation-in-part of application Ser. No. 373,633, filed Apr. 30, 1982.

TECHNICAL FIELD

This invention relates to nitroarylacetic acid esters and derivatives thereof—more particularly to processes for preparing the esters and derivatives.

BACKGROUND

As disclosed in U.S. Pat. No. 3,600,437 (Marshall), it is known that 2-(3-phenoxybenzene)propionic acid—commonly known as fenoprofen—and related compounds are pharmaceutically-active materials that can be prepared by the techniques taught in that patent. Those techniques have the disadvantage of being tedious and time-consuming, as well as using starting materials that are not as economical and readily-available as might be desired.

It is known that nitrobenzene acetic acids and their esters are particularly useful intermediates for the synthesis of pharmaceuticals. For example, 2-[4-(1,3-dihydro-1-oxo-2H-isoindol-2-yl)phenyl]propionic acid—an anti-inflammatory and analgesic agent commonly known as indoprofen—can be prepared from a 2-(4-nitrobenzene)propionic acid intermediate by hydrogenating the intermediate, reacting the resultant 2-(4-aminobenzene)propionic acid with phthalic anhydride, and reducing the resultant 2-(4-phthalimidophenyl)propionic acid, e.g., with zinc and formic acid. Also, 2-[4-(1,3-dihydro-1-oxo-2H-isoindol-2-yl)phenyl]butyric acid—commonly known as indobufen—can be formed in a similar manner from 2-(4-nitrobenzene)butyric acid.

In the past, a disadvantage of employing nirobenzene acetic acid or esters as pharmaceutical intermediates has been the difficulty of preparing those intermediates by conventional techniques. For example, 2-(4-nitrobenzene)propionic acid has been customarily formed by a three-step procedure wherein (1) 4-ethylnitrobenzene is reacted with sodium phenoxide and carbon dioxide to produce disodium 2-methyl-2-(4-nitrobenzene)malonate, (2) the malonate salt is converted by acidification into the corresponding diacid, and (3) the diacid is heated to effect decarboxylation.

It would obviously be a welcome contribution to the art to provide a method of synthesizing nitrobenzeneacetic acid esters, including nitrophenoxybenzeneacetic acid esters, and derivatives thereof in a simple, straightforward manner.

SUMMARY OF INVENTION

An object of this invention is to provide novel processes for preparing nitrophenoxy- or nitrophenylthiobenzeneacetic acid esters.

Another object is to provide such processes which permit the preparation of the esters in good yield with high selectivity in a very simple and straightforward manner.

A further object is to provide novel, improved processes for preparing derivatives of nitrophenoxy- or nitrophenylthiobenzeneacetic acid esters.

These and other objects are attained by (A) reacting a nitrophenoxy- or nitrophenylthiobenzene with an alpha,alpha-disubstituted acetic acid ester in an inert solvent and in the presence of a base so as to form a nitrophenoxy- or nitrophenylthiobenzeneacetic acid ester and (B) when appropriate, converting the nitrophenoxy- or nitrophenylthiobenzeneacetic acid ester to a desired derivative thereof.

DETAILED DESCRIPTION

Nitrophenoxy- and nitrophenylthiobenzenes utilizable in the practice of the invention are compounds corresponding to the formula:

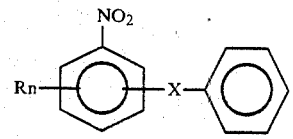

wherein X is oxygen or sulfur; R is an inert substituent, i.e., any substituent that does not interfere with the desired reaction, such as nitro, halo, alkoxy, haloalkyl, methanesulfonyl, methanesulfonamido, acetamido, methylmercapto, etc.; n has a value of 0-3; and there is a replaceable hydrogen in a position ortho or para, preferably para, to the carbon bearing the nitro substituent. The preferred reactant is 2-phenoxynitrobenzene, which is ideally suited for the synthesis of fenoprofen.

The alpha,alpha-disubstituted acetic acid esters that can be used in the practice of the invention include a variety of such compounds, which—in general—may be represented by the formula:

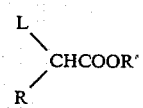

wherein L is a leaving group; R is a hydrocarbyl (e.g., alkyl, alkenyl, alkynyl, cycloalkyl, cycloalkenyl, aryl, aralkyl, etc.) or hydrocarbyloxyhydrocarbyl (e.g., alkoxyalkyl, aryloxyalkyl, alkoxyaryl, alkoxycycloalkyl, etc.) group which most preferably contains up to about 10 carbons; and R' is a hydrocarbyl group which preferably contains up to about 10 carbons and most preferably is an alkyl group.

Exemplary leaving groups, L, include halo, aryloxy, haloaryloxy, alkylthio, cycloalkylthio, arylthio, aralkylthio, haloalkylthio, halocycloalkylthio, haloarylthio, haloaralkylthio, or—less preferably—alkoxy, cycloalkoxy, aralkoxy, haloalkoxy, halocycloalkoxy, haloaralkoxy, and the like, as well as other suitable leaving groups which have been described in the literature, e.g., in Golinski et al., "'Vicarious' Nucleophilic Substitution of Hydrogen in Aromatic Nitro Compounds," *Tetrahedron Letters*, Vol. 37, pp. 3495-8 (1978); Makosza et al., "Vicarious Substitution of Hydrogen in Aromatic Nitro Compounds with Acetonitrile Derivatives," *Journal of Organic Chemistry*, Vol. 45, pp. 1534-5 (1980); and Makosza, "Some New Reactions of Carbanions. Vicarious Nucleophilic Substitution of Hydrogen in Nitroarenes," *Int. Conf. Chem. Biotechnol. Biol. Act. Nat. Prod. (Proc.)*, 1st, 1982, issue 2, pp. 480-490.

When the leaving group is an organic group, it is generally preferred that the group contain not more than about 10 carbons, although organic leaving groups having an even higher carbon content are satisfactory in the practice of the invention. Preferably, the leaving group is halo, i.e., chloro, bromo, fluoro, or iodo; and it is more preferably chloro or bromo, most preferably chloro.

Exemplary of utilizable alpha,alpha-disubstituted acetic acid esters are alpha-chloropropionates such as methyl, ethyl, propyl, isopropyl, butyl, t-butyl, cyclohexyl, phenyl, and benzyl 2-chloropropionates; the corresponding alpha-bromopropionates; and other alpha-substituted monocarboxylic acid esters such as methyl 2-methylmercaptopropionate; ethyl 2-butylmercaptopropionate, methyl 2-phenoxybutyrate, phenyl 2-methylmercaptopropionate, butyl 2-cyclohexylmercaptovalerate, methyl 2-(4-fluorophenoxy)propionate, and the like. The alpha-halo acid esters, i.e., esters of alpha-halomonocarboxylic acids containing at least three carbons, are especially preferred, although similar esters in which the alpha-halo substituent is replaced by one of the other leaving groups mentioned above are also highly desirable.

The solvent used in a nitrophenoxy- or nitrophenylthiobenzene/ester reaction of the invention may be any solvent that is inert under the conditions of the reaction, i.e., any solvent that will not prevent the reaction from occurring. Such solvents are substantially anhydrous and are generally aprotic, although solvents such as liquid ammonia are also utilizable.

Illustrative aprotic solvents which may be employed in the process of the invention include ethers such as diethyl ether, dibutyl ether, 1-ethoxyhexane, tetrahydrofuran, 1,4-dioxane, 1,3-dioxolane, diglyme, 1,2-diethoxyethane, anisole, etc.; tertiary amines such as pyridine, N-ethylpiperidine, triethyl amine, tributyl amine, N,N-diphenyl-N-methyl amine, N,N-dimethylaniline, etc.; and other aprotic solvents. However, the preferred aprotic solvents are dipolar aprotic solvents such as dimethyl sulfoxide, N,N-dimethylformamide, N,N-dimethylacetamide, dimethyl sulfone, tetramethylene sulfone, N-methylpyrrolidinone, and the like.

Bases useful in the practice of the invention include all bases strong enough to activate the ester reactant, e.g., alkaline earth metal compounds such as calcium oxide, calcium hydride, calcium hydroxide, barium oxide, barium hydroxide, magnesium hydroxide, zinc hydroxide, etc. However, the base is preferably an alkali metal compound, e.g., an organoalkali metal compound, alkali metal hydride, alkali metal hydroxide, alkali metal oxide, alkali metal amide, or alkali metal alcoholate, such as butyllithium, phenyllithium, ethylsodium, amylsodium, butylpotassium, benzylpotassium, sodium dimsylate (i.e., the sodium salt of diethylsulfoxide), sodium hydride, potassium hydride, sodium hydroxide, potassium hydroxide, sodium oxide, potassium oxide, sodium amide, potassium amide, lithium diisopropylamide, sodium methoxide, potassium t-butoxide, the sodium salt of the monomethylether of ethylene glycol, sodium phenoxide, and the like. Ordinarily the use of sodium hydride, potassium hydride, or potassium t-butoxide will be found most convenient and economical.

Use of an alkali metal compound as the base permits the alternatives of using the alkali metal compound alone or in conjunction with a phase transfer catalyst, such as a quaternary ammonium salt, ethylene glycol, or a suitable crown ether. When a phase transfer catalyst is employed (1) the alkali metal compound may be any of the alkali metal compounds generically or specifically indicated above, although the type of alkali metal compound being used determines the type of crown ether that is preferably utilized—lithium base generally calling for the use of a 12-crown-4 ether, sodium bases generally calling for the use of a 15-crown-5 ether, and potassium bases generally calling for the use of an 18-crown-6 ether, and (2) the reaction medium may be any of the aprotic solvents mentioned above, or it may be an inert liquid hydrocarbon such as benzene, toluene, xylene, hexane, heptane, isooctane, or the like.

When the alkali metal hydride, especially a highly pure alkali metal hydride, is employed as the base, it is desirable to include a small amount of a transfer agent such as water, alcohol, or the like in the system. It is believed that the transfer agent activates the hydride by reacting therewith to form a small amount of the alkali metal hydroxide or alcoholate.

The nitrophenoxy- or nitrophenylthiobenzeneacetic acid ester synthesis of the invention appears to occur by a nucleophilic substitution mechanism whereby the ester undergoes a nucleophilic substitution on an unsubstituted ring carbon of the nitrophenoxy- or nitrophenylthiobenzene during which the alpha-substituent of the acetic acid ester functions as a leaving group. It is conducted in a substantially anhydrous reaction system, and accordingly, except when a small amount of water (which is itself consumed by reaction with the alkali metal hydride) is employed as a transfer agent, the components of the reaction system should be brought together and maintained under a dry inert atmosphere. Thus, while it is possible to conduct the process in the presence of air, it is desirable to maintain the reaction system under an atmosphere of dry nitrogen or the like. Since the reaction itself is normally an exothermic reaction, with its initiation readily ascertainable by noting the exotherm produced, the reactants are ordinarily brought together at ambient temperatures, although the temperature may be raised or lowered to suit the needs of the occasion if desired.

The nitrophenoxy- or nitrophenylthiobenzene and alpha, alpha-disubstituted acetic acid ester may be used in amounts such as to provide a stoichiometric excess of either of the reactants or the stoichiometric amount of each. However, when a stoichiometric excess of the nitrophenoxy- or nitrophenylthiobenzene is employed, the quantity of product obtainable will be limited by the quantity of ester used, so it is desirable to utilize a stoichiometric excess of the ester. The amount of base employed is preferably such as to provide at least two molar equivalents of base per mol of nitrophenoxy- or nitrophenylthiobenzene, since the use of smaller amounts—although permitting the reaction to occur—makes the base of the limiting reagent.

The mode of addition of the ingredients of the reaction system is not particularly critical. Accordingly, it is convenient to add the nitrophenoxy- or nitrophenylthiobenzene to a mixture of the other materials, add the base to a mixture of the other materials, add the reactants to a mixture of the base and inert solvent, introduce all four ingredients simultaneously into the reaction zone, or the like. Since the reaction ordinarily proceeds very rapidly, long reaction times are not required. The reaction will usually be completed within a matter of minutes or a few hours at ambient temperatures.

When derivatives of the nitroarylacetic acid esters are desired, they may be prepared by employing conventional techniques to convert to the desired derivatives the nitrophenoxy- or nitrophenylthiobenzeneacetic acid esters made in accordance with the present invention. Thus, for example:

(A) an alkyl 2-(4-nitro-3-phenoxybenzene)propionate synthesized by the process of this invention may be hydrolyzed to 2-(4-nitro-3-phenoxybenzene)propionic acid, which in turn may be hydrogenated to 2-(4-amino-3-phenoxybenzene)propionic acid, which may then be deaminated to fenoprofen, and (B) an alkyl 2-(4-nitro-3-phenoxybenzene)propionate synthesized by the process of this invention may be hydrogenated to an alkyl 2-(4-amino-3-phenoxybenzene)propionate, which in turn may be deaminated to form an alkyl 2-(3-phenoxybenzene)propionate, which may then be hydrolyzed to fenoprofen, etc.

The particular conventional techniques used to convert the nitrophenoxy- or nitrophenylthiobenzeneacetic acid esters into their various derivatives are not critical. It may sometimes be desirable to use certain particular techniques for the preparation of the derivatives, e.g., the reduction and/or hydrolysis techniques taught in March, *Advanced Organic Chemistry*, McGraw-Hill, New York, 1977, pages 809-10, 1125-6, and the references cited therein, the disclosures of which are incorporated herein by reference. However, the overall processes for preparing the derivatives are simplified and made more efficient and economical by the present simplification of the synthesis of the nitrophenoxy- or nitrophenylthiobenzeneacetic acid esters, regardless of the particular techniques used to convert them into their various derivatives.

As indicated above, the present invention is particularly advantageous in providing a readier and more economical route to the synthesis of pharmaceuticals and other chemical products that can be prepared from nitrophenoxy- or nitrophenylthiobenzeneacetic acid esters, most notably fenoprofen.

The following example is given to illustrate the invention and is not intended as a limitation thereof.

EXAMPLE

Part A

A solution of 2.9 g (26 mmols) of potassium t-butoxide in 20 ml of N,N-dimethylformamide (DMF) in a flame-dried flask under nitrogen was cooled with an ice water bath. Then a solution of 3.0 g (13 mmols) of 93% 2-phenoxynitrobenzene and 1.6 g (13 mmols) of methyl 2-chloropropionate in 2.0 ml of DMF was added dropwise. The resulting purple mixture was stirred at 0°–5° C. for 15 minutes and poured into 200 ml of 1N HCl. The aqueous mixture was extracted with three 150 ml portions of diethyl ether. The ether layers were combined, dried over magnesium sulfate, and concentrated to give 6.0 g of red oil. Chromatography of this oil on 100 g of silica gel (230–400 mesh) with 40% dichloromethane/60% petroleum ether (b.p. 35°–60° C.) as eluent afforded a fraction containing 2.2 g (56%) of methyl 2-(4-nitro-3-phenoxybenzene)propionate.

Part B

A mixture of 1.0 g of methyl 2-(4-nitro-3-phenoxybenzene)propionate, 0.1 g of 7% palladium on carbon, and 20 ml of absolute ethanol was hydrogenated at 50 psig hydrogen pressure for one hour, filtered, and concentrated to give 0.96 g of oil. Thin layer chromatographic and NMR analyses of this oil showed that it contained only methyl 2-(4-amino-3-phenoxybenzene)propionate.

Part C

A solution of 0.20 g (0.74 mmol) of methyl 2-(4-amino-3-phenoxybenzene)propionate in 1.0 ml of dry tetrahydrofuran (THF) was added dropwise to a refluxing solution of 0.18 ml (1.3 mmols) of isoamyl nitrite in 4.0 ml of THF. The resulting mixture was heated at reflux for 1.5 hours, cooled to room temperature, and concentrated. The residue was subjected to preparative thin layer chromatography to yield 0.032 g (16%) of methyl 2-(3-phenoxybenzene)propionate.

This invention is susceptible to considerable variation within the spirit and scope of the appended claims.

We claim:

1. A process which comprises reacting a nitrophenoxy- or nitrophenylthiobenzene with an alpha,alpha-disubstituted acetic acid ester in an inert solvent and in the presence of a base so as to form a nitrophenoxy- or nitrophenylthiobenzeneacetic acid ester.

2. The process of claim 1 wherein the nitrophenoxy- or nitrophenylthiobenzene is 2-phenoxynitrobenzene.

3. The process of claim 1 wherein the alpha,alpha-disubstituted acetic acid ester is an alpha-halomonocarboxylic acid ester containing at least three carbons in the acid moiety.

4. The process of claim 3 wherein the alpha-halomonocarboxylic acid ester is an alpha-chloro or alpha-bromomonocarboxylic acid ester.

5. The process of claim 4 wherein the alpha-halomonocarboxylic acid ester is an alkyl alpha-chloropropionate.

6. The process of claim 1 wherein the solvent is an aprotic solvent.

7. The process of claim 6 wherein the solvent is a dipolar aprotic solvent.

8. The process of claim 1 wherein the base is an alkali metal compound.

9. The process of claim 8 wherein the base is potassium t-butoxide.

10. The process of claim 1 wherein (A) a nitrophenoxy- or nitrophenylthiobenzene is reacted with an alpha,alpha-disubstituted acetic acid ester in an inert solvent and in the presence of a base so as to form a nitrophenoxy- or nitrophenylthiobenzeneacetic acid ester and (B) the nitrophenoxy- or nitrophenylthiobenzeneacetic acid ester is hydrolyzed to a nitrophenoxy- or nitrophenylthiobenzeneacetic acid.

11. The process of claim 10 wherein (A) a nitrophenoxy- or nitrophenylthiobenzene is reacted with an alpha,alpha-disubstituted acetic acid ester in an inert solvent and in the presence of a base so as to form a nitrophenoxy- or nitrophenylthiobenzeneacetic acid ester, (B) the nitrophenoxy- or nitrophenylthiobenzeneacetic acid ester is hydrolyzed to a nitrophenoxy- or nitrophenylthiobenzeneacetic acid, and (C) the nitrophenoxy- or nitrophenylthiobenzeneacetic acid is hydrogenated to an aminophenoxy- or aminophenylthiobenzeneacetic acid.

12. The process of claim 11 wherein (A) a nitrophenoxy- or nitrophenylthiobenzene is reacted with an alpha,alpha-disubstituted acetic acid ester in an inert solvent and in the presence of a base so as to form a nitrophenoxy- or nitrophenylthiobenzeneacetic acid ester, (B) the nitrophenoxy- or nitrophenylthiobenzenepropionic acid ester is hydrolyzed to a nitrophenoxy- or nitrophenylthiobenzeneacetic acid, (C) the nitrophenoxy- or nitrophenylthiobenzeneacetic acid is hydrogenated to an aminophenoxy- or aminophenylthiobenzeneacetic acid, and (D) the aminophenoxy- or aminophenylthiobenzeneacetic acid is deaminated to a phenoxy- or phenylthiobenzeneacetic acid.

13. The process of claim 12 wherein (A) 2-phenoxynitrobenzene is reacted with an alkyl alpha-chloropropionate in an inert solvent and in the presence of a base so as to form an alkyl 2(4-nitro-3-phenoxybenzene)propionate, (B) the alkyl 2-(4-nitro-3-phenoxybenzene)propionate is hydrolyzed to 2-(4-nitro-3-phenoxybenzene)propionic acid, (C) the 2-(4-nitro-3-phenoxybenzene)propionic acid is hydrogenated to 2-(4-amino-3-phenoxybenzene)propionic acid, and (D) the 2-(4-amino-3-phenoxybenzene)propionic acid is deaminated to 2-(3-phenoxybenzene)propionic acid.

14. The process of claim 1 wherein (A) a nitrophenoxy- or nitrophenylthiobenzene is reacted with an alpha,alpha-disubstituted acetic acid ester in an inert solvent and in the presence of a base so as to form a nitrophenoxy- or nitrophenylthiobenzeneacetic acid ester and (B) the nitrophenoxy- or nitrophenylthiobenzeneacetic acid ester is hydrogenated to an aminophenoxy- or aminophenylthiobenzeneacetic acid ester.

15. The process of claim 14 wherein (A) is nitrophenoxy- or nitrophenylthiobenzene is reacted with an alpha,alpha-disubstituted acetic acid ester in an inert solvent and in the presence of a base so as to form a nitrophenoxy- or nitrophenylthiobenzeneacetic acid ester, (B) the nitrophenoxy- or nitrophenylthiobenzeneacetic acid ester is hydrogenated to an aminophenoxy- or aminophenylthiobenzeneacetic acid ester, and (C) the aminophenoxy- or aminophenylthiobenzeneacetic acid ester is deaminated to a phenoxy- or phenylthiobenzeneacetic acid ester.

16. The process of claim 15 wherein (A) a nitrophenoxy- or nitrophenylthiobenzene is reacted with an alpha,alpha-disubstituted acetic acid ester in an inert solvent and in the presence of a base so as to form a nitrophenoxy- or nitrophenylthiobenzeneacetic acid ester, (B) the nitrophenoxy- or nitrophenylthiobenzenepropionic acid ester is hydrogenated to an aminophenoxy- or aminophenylthiobenzenepropionic acid ester, (C) the aminophenoxy- or aminophenylthiobenzeneacetic acid ester is deaminated to a phenoxy- or phenylthiobenzeneacetic acid ester, and (D) the phenoxy- or phenylthiobenzeneacetic acid ester is hydrolyzed to a phenoxy- or phenylthiobenzeneacetic acid.

17. The process of claim 16 wherein (A) 2-phenoxynitrobenzene is reacted with an alkyl alpha-chloropropionate in an inert solvent and in the presence of a base so as to form an alkyl 2-(4-nitro-3-phenoxybenzene)propionate, (B) the alkyl 2-(4-nitro-3-phenoxybenzene)propionate is hydrogenated to an alkyl 2-(4-amino-3-phenoxybenzene)propionate, (C) the alkyl 2-(4-amino-3-phenoxybenzene)propionate is deaminated to an alkyl 2-(3-phenoxybenzene)propionate, and (D) the alkyl 2-(3-phenoxybenzene)propionate is hydrolyzed to 2-(3-phenoxybenzene)propionic acid.

* * * * *